United States Patent [19]

Kotler et al.

[11] Patent Number: 5,722,396
[45] Date of Patent: Mar. 3, 1998

[54] METHOD FOR ESTIMATING CREATININE CLEARANCE USING MEASUREMENTS OF BODY CELL MASS

[75] Inventors: Donald P. Kotler, New Rochelle; Emilia M. Sordillo, New York, both of N.Y.

[73] Assignee: St. Luke's-Roosevelt Hospital Center, New York, N.Y.

[21] Appl. No.: 694,615

[22] Filed: Aug. 13, 1996

[51] Int. Cl.$^6$ .................................................. A61B 5/05
[52] U.S. Cl. .................................. 128/630; 128/734
[58] Field of Search ................................ 128/630, 734, 128/774, 898

[56] References Cited

U.S. PATENT DOCUMENTS

| | | | |
|---|---|---|---|
| 4,880,014 | 11/1989 | Zarowitz et al. | 128/734 |
| 4,911,175 | 3/1990 | Shizgal | 128/734 |
| 5,100,646 | 3/1992 | Choyke et al. | 424/9 |
| 5,301,673 | 4/1994 | Rabito et al. | 128/659 |
| 5,500,372 | 3/1996 | Kell | 430/98 |
| 5,615,689 | 4/1997 | Kotler | 128/734 |

OTHER PUBLICATIONS

D. Gilbert, "Aminoglycosides," *Mandel, Douglas and Bennet's Principles and Practice of Infectious Diseases* (4th ed. 1995), pp. 279–306.

J. Bertino, Jr. et al., "Incidence of and Significant Risk Factors for Aminoglycoside–Associated Nephrotoxicity in Patients Dosed by Using Individualized Pharmacokinetic Monitoring," *J. Infectious Diseases* (1993), vol. 167, pp. 173–179.

R. Sladen, "Accurate estimation of glomerular filtration in the intensive care unit: Another Holy Grail?," *Crit. Care Med.* (1993), vol. 21, No. 10, pp. 1424–1427.

B. Kasiske et al., "Laboratory Assessment of Renal Disease: Clearance, Urinalysis and Renal Biopsy," *The Kidney* (5th ed. 1991), pp. 1137–1174.

W. Schiller et al., "Creatinine and Nitrogen Excretion In Seriously Ill and Injured Patients," *Surg. Gyn. & Ob.* (1979), vol. 149, pp. 561–566.

S. Robert et al., "Predictability of creatinine clearance estimates in critically ill patients," *Crit. Care Med.* (1993), vol. 21, No. 10, pp. 1487–1495.

C. Martin et al., "Assessment of creatinine clearance in intensive care patients," *Crit. Care Med.* (1990), vol. 18, No. 11, pp. 1224–1226.

R. Skinner et al., "Inaccuracy of glomerular filtration rate estimation from height/plasma creatinine ratio," *Archives of Disease in Childhood* (1994), vol. 70, pp. 387–390.

T. Wolever, "Effect of Meal Frequency On Serum Amino Acids and Creatinine Clearance In Young Men," *Am J. Med. Sci.* (1994), vol. 307, No. 2, pp. 97–101.

E. Boyce et al., "Creatinine clearance estimation in protein–malnourished patients," *Clin. Pharm.* (1989), vol. 8, pp. 721–726.

K. Siersback–Nielsen et al., "Rapid Evaluation of Creatinine Clearance," *The Lancet* (1971), vol. 1, pp. 1133–1134.

R. Jelliffe, "Creatinine Clearance: Bedside Estimate," *Annuals of Internal Medicine* (1973), vol. 79, No. 4, pp. 604–605.

D. Cockcroft & M. Gault, "Prediction of Creatinine Clearance from Serum Creatinine," *Nephron* (1976), vol. 16, pp. 31–41.

T. Bjornsson, "Use of Serum Creatinine Concentrations to Determine Renal Function," *Clin. Pharmacokinetics* (1979), vol. 4, pp. 200–202.

G. Gates, "Creatinine Clearance Estimation from Serum Creatinine Values: An Analysis of Three Mathematical Models of Glomerular Function," *Am. J. Kidney Diseases* (1985), vol. 5, No. 3, pp. 199–205.

T. Hallynck et al., "Prediction of Creatinine Clearance from Serum Creatinine Concentration Based on Lean Body Mass," *Clin. Pharmacol. Ther.* (1981), vol. 30, No. 3, pp. 414–421.

M., O'Connell et al., "Predictive Performance of Equations to Estimate Creatinine Clearance in Hospitalized Elderly Patients," *Ann. Pharmacother.* (1992), vol. 26, pp. 627–635.

M. Smythe et al., "Estimating creatinine clearance in elderly patients with low serum creatinine concentrations," *Am. J. Hosp. Pharm.* (1994), vol. 51, pp. 198–204.

J. Bertino, Jr., "Measured Versus Estimated Creatinine Clearance in Patients With Low Serum Creatinine Values," *Ann. Pharmacther.* (1993), vol. 27, pp. 1439–1441.

L. Caregaro et al., "Limitations of Serum Creatinine Level and Creatinine Clearance as Filtration Markers in Cirrhosis," *Arch. Intern. Med.* (1994), vol. 154, pp. 201–205.

M. Chrymko & J. Schentag, "Creatinine Clearance Predicitons in Acutely Ill Patients," *Am. J. Hosp. Pharm.* (1981), vol. 38, pp. 837–840.

R. Dionne et al., "Estimating Creatinine Clearance in Morbidly Obese Patients," *Am. J. Hosp. Pharm.* (1981), vol. 38, pp. 841–844.

A. Lau et al., "Estimation of Creatinine Clearance in Malnourished Patients," *Clin. Pharm.* (1988), vol. 7, pp. 62–65.

W. Sawyer et al., "Variables Affecting Creatinine Clearance Prediction," *Am. J. Hosp. Pharm.* (1983), vol. 40, pp. 2175–2180.

W. Sawyer et al., "A Multicenter Evaluation of Variables Affecting the Predictibility of Creatinine Clearance," *Am. J. Clin. Path.* (1982), vol. 78, No. 6, pp. 832–838.

K. Segal et al., "Lean body mass estimation by bioelectric impedance analysis: a four site cross–validation study," *Am. J. Clin. Nutr.* (1988), vol. 47, pp. 7–14.

(List continued on next page.)

*Primary Examiner*—Francis Jaworski
*Attorney, Agent, or Firm*—Baker & Botts, LLP

[57] ABSTRACT

Creatinine clearance is estimated in a patient by determining his or her body cell mass. In turn, the body cell mass of the patient is measured using bioimpedance analysis techniques. The determined value of body cell mass is normalized by the height$^2$ of the patient. The body cell mass or its normalized value provides an indication of actual creatinine clearance in the subject through use of a predictive formula. From this prediction, accurate dosages of potentially nephrotoxic medications can be appropriately prescribed.

10 Claims, No Drawings

OTHER PUBLICATIONS

K. Segal et al., "Estimation of Human Body Composition by Electrical Impedance Methods: a comparative study," *J. Appl. Physiol. Soc'y*, (1985), vol. 58, pp. 1565–1571.

H. Lukaski et al., "Assessement of fat–free mass using bioelectrical impedance measurements of the human body," *Am. J. Clin. Nutr.* (1985), vol. 41, pp. 810–817.

R. Kushner & D. Schoeller, "Estimation of total body water by bioelectrical impedance analysis," *Am. J. Clin. Nutr.* (1986), vol. 44, pp. 417–421.

M. Smythe et al., "Relationship Between Values of Bioelectrical Impedance and Creatinine Clearance," *Pharmacotherapy* (1990), vol. 10, No. 1, pp. 42–46.

J. Bland et al., "Statistical Methods for Assessing Agreement Between Two Methods of Clinical Measurement," *The Lancet* (1986), vol. 1, pp. 307–310.

METHOD FOR ESTIMATING CREATININE CLEARANCE USING MEASUREMENTS OF BODY CELL MASS

FIELD OF THE INVENTION

The present invention relates to a method for estimating creatinine clearance in human subjects which is particularly suitable for determining appropriate dosages of medication so as to avoid or prevent adverse drug reactions and toxicity.

BACKGROUND INFORMATION

Dosing regimens for several drugs used in treating renal diseases, most notably the aminoglycosides, are based upon a measurement of renal function known as the glomerular filtration rate (GFR). It is often necessary to estimate GFR, since actual measurement is both expensive and time-consuming. However, standard methods for estimating renal function are prone to errors which can result in inaccurate drug dosages being prescribed to an individual. These inaccuracies have created substantial risk of nephrotoxicity in underweight patients and insufficient dosages being prescribed to overweight subjects.

The reported incidence of aminoglycoside nephrotoxicity ranges from 0–50%, with rates in most studies in the 5–25% range. Prospective studies that defined nephrotoxicity as a substantial decrease in the GFR reported an incidence of nephrotoxicity that ranged from 5–10% in severely ill patients. Aminoglycoside toxicity can be minimized if such drugs are dosed appropriately.

In clinical practice, renal function can be estimated through measurement of inulin clearance ($CL_{IN}$) or creatinine clearance ($CL_{CR}$). Measurement of inulin clearance is preferred by many because inulin is an inert sugar that is cleared solely by glomerular filtration. Inulin is neither secreted nor absorbed by the renal tubules, making it a relatively accurate indicator of GFR.

However, measurements of $CL_{IN}$ can vary by as much as 20% in an individual at a given time. In addition, determination of inulin clearance is not practical in an everyday clinical setting. The procedure requires intravenous infusion of inulin followed by three timed urine collections. Thus, measurement of inulin clearance is laborious, time-consuming and expensive.

Measurement of creatinine clearance is a practical substitute for inulin clearance in estimating renal function. Creatinine is a product of muscle metabolism. It is eliminated mainly by glomerular filtration, but also to a minor extent by tubular secretion. For this reason, $CL_{CR}$ measurements usually overestimate the glomerular filtration rate in comparison to $CL_{IN}$. However, $CL_{CR}$ measurement is simpler and less expensive to perform.

There are several methods for estimating $CL_{CR}$. The standard method involves collecting the urine output ($V_U$) from a subject for a 24-hour period and measuring urine ($U_{CR}$) and serum ($S_{CR}$) creatinine concentrations. Creatinine clearance is then calculated as:

$$CL_{CR} = (U_{CR})(V_U)/(S_{CR})$$

Some studies suggest that shorter collection periods (i.e. 30 minutes or two hours) are as predictive of GFR as the 24-hour collection period. However, many patients who are admitted to a hospital require urgent administration of aminoglycosides or other potentially toxic medications in a time frame that does not allow for such measurements of $CL_{CR}$.

Because of this, a number of authors have developed mathematical equations to estimate GFR. The equation that is most commonly used in clinical practice is the Cockcroft-Gault (C-G) equation. The equation for male subjects is expressed as:

Estimated Male $CL_{CR} = [(140-age) \times IBW/(72 \times S_{CR})]$ where IBW and age refer to a patient's ideal body weight (kg) and physical age, respectively. For female subjects, the C-G equation is:

Estimated Female $CL_{CR} = (0.85 \times \text{Estimated male } CL_{CR})$.

In turn, ideal body weight is calculated as:

Male $IBW$ (kg)=50 +[2.3×(Height in inches −60)]

Female $IBW$ (kg)=45 +[2.3×(Height in inches −60)]

The C-G equations assume that a subject is in a steady-state, that skeletal mass is a constant percentage of weight and that deviations from ideal weight do not affect renal function. However these assumptions may not be true, particularly in cases where a patient is malnourished or severely ill, thereby diminishing the accuracy of renal function determination using the C-G equations. It has been determined, in fact, that the C-G equations are prone to error, especially where a subject's body weight varies from his or her ideal body weight.

Moreover, individual variables in the equation such as age, $S_{CR}$, IBW, height and sex do not correlate with measured $CL_{CR}$. Actual body weight as a percent of ideal, however, correlated with $CL_{CR}$, suggesting that the C-G equations systematically overestimate $CL_{CR}$ in subjects below IBW and underestimate $CL_{CR}$ in subjects over IBW. A physician relying on these equations would, thus, over-prescribe medication for underweight subjects and under-prescribe medications in overweight patients.

Substitution of actual weight for ideal weight in the C-G equation somewhat improved the prediction of $CL_{CR}$. Still, published case series have reported an incidence of aminoglycoside nephrotoxicity ranging from 0 to 25% based upon use of the C-G equations. In light of this, several other authors have made attempts at improving predictive formulae.

Boyce et al. concluded that the C-G equation used with the lower of either ideal or actual weights was the most precise and least biased method for testing malnourished patients. E. G. Boyce et al., *Creatinine Clearance Estimation in Protein-Malnourished Patients*, 8 Clin. Pharm. 721, 726 (1989).

M. Smythe et al. concluded that in elderly patients with low $S_{CR}$, correcting serum creatinine in the C-G equations to 1.0 mg/dL led to underestimates of both $CL_{CR}$ and the dosages of aminoglycosides. M. Smythe et al., *Estimating Creatinine Clearance in Elderly Patients with Low Serum Creatinine Concentrations*, 51 Am. J. Hosp. Pharm. 198, 204 (1994).

O'Connell et al. found the Jelliffe 1973 equation using modified lean body weight was best for predicting the correct drug doses for hospitalized elderly patients. M. B. O'Connell et al., *Predictive Performance of Equations to Estimate Creatinine Clearance in Hospitalized Elderly Patients*, 26 Ann. Pharmacother. 627, 635 (1992).

Bertino concluded that in patients with an $S_{CR}$ of less than 1.0 mg/dL, the actual $S_{CR}$ level should be used when calculating $CL_{CR}$ by the C-G equations. J. S. Bertino, Jr., *Measured Versus Estimated Creatinine Clearance in*

*Patients with Low Serum Creatinine Values*, 27 Ann. Pharmacother. 1439, 1441 (1993).

Of all the studies in this field, only two others are known to have used bioimpedance analysis (BIA) to predict $CL_{CR}$. The first group, A. S. Smythe et al., performed BIA on 28 healthy adult volunteers. They measured $CL_{CR}$ using 24-hour urine collection and calculated $CL_{CR}$ using seven predictive formulas.

Multiple linear regression analysis of their findings revealed that measured $S_{CR}$ and resistance (R), determined by BIA were significant predictors of measured $CR_{CL}$. The authors derived a predictive equation:

$$CL_{CR} = 288.3 - 0.202(R) - 66.64(S_{CR})$$

The mean absolute prediction error for $CL_{CR}$ determined by this method was significantly lower than those obtained from 4 of 7 standard $CL_{CR}$ predictive equations. A. S. Smythe et al., *Relationship Between Values of Bioelectrical Impedance and Creatinine Clearance*, 10 Pharmacotherapy 42, 46 (1990).

In the second study, Robert et al. used inulin clearance as the criterion method for GFR, then calculated $CL_{CR}$ using 30-minute and 24-hour urine collection techniques. The authors utilized BIA to measure lean body mass (LBM) and then used LBM in place of weight in the C-G equation to predict $CL_{CR}$ with a corrected $S_{CR}$.

In this latter study, LBM and a corrected $S_{CR}$ tended to overestimate the GFR. Their research concluded that equations using the lower of IBW or actual body weight (ABW) along with a corrected $S_{CR}$ were significantly better predictors of inulin clearance than either the 30-minute or 24-hour urine collection techniques. However, their results indicate a greater than 20% disparity between the modified C-G equations and $CL_{IN}$ in 55% of their subjects. S. Robert et al., *Predictability of Creatinine Clearance Estimates in Critically Ill Patients*, 21 Crit. Care Med. 1487, 1495 (1993).

With the inconclusive and varied results above, the issues of how to best express weight in the calculation and whether or not to correct $S_{CR}$ in the C-G equations remain unresolved. Furthermore, no equations have yet been determined which can apply to all groups of patients, regardless of such factors as age, race, gender, nutritional status, or those affected by disease. Improving the prediction of $CL_{CR}$ could decrease the incidence of nephrotoxicity independent of dosing frequency, which could in turn lead to cost savings in medical care.

BRIEF SUMMARY OF THE INVENTION

In accordance with the present invention, a method for predicting creatinine clearance in one or more patients is disclosed whereby body cell mass (BCM) is measured to estimate creatinine clearance. BCM is determined by performing bioimpedance analysis (BIA) on a subject and using the results to calculate BCM according to previously derived formulas. Additionally, the height of a subject may also be measured.

BCM has a strong correlation with measured $CL_{CR}$ in comparison to actual body weight. Body Cell Mass Index (BCMI), which is the body cell mass of the subject normalized by his or her height$^2$, provides the strongest correlation to measured creatinine clearance. An estimate of creatinine clearance can then be determined directly from the calculation of BCM.

An object of the present invention is to provide a method for estimating the creatinine clearance of a patient which is more accurate than other known methods for such estimation.

A further object of the present invention is to provide a method for estimating the creatinine clearance which is clinically practical and more accommodating than actual creatinine clearance measurement.

A still further object of the present invention is to provide a method for determining creatinine clearance which is independent of such variables as the patient's age, race, gender, actual or ideal body weight, nutritional status, or affliction with disease.

A still further object of the present invention is to provide a method for creatinine clearance which allows for proper dosing of potentially nephrotoxic or other medications in the treatment of renal disease.

Further objects of the invention will readily appear to those skilled in the art from a review of the invention as disclosed.

DETAILED DESCRIPTION OF THE INVENTION

A study was performed using 26 subjects, including 13 men and 13 women. Nine subjects were HIV-infected and had chronic gastrointestinal disease with malabsorption, while 17 subjects were normal controls. The goal of the study was to determine a more accurate method for estimating creatinine clearance and for determining the accuracy of the Cockcroft-Gault equations in determining creatinine clearance in patients whose weight varies from ideal.

Study participants had no history of primary renal disease and were not receiving nephrotoxic drugs. Subjects ages ranged from 27 to 63 years and their weights varied from 56 to 194% of ideal. $S_{CR}$ ranged from 44.2–123.8 µmol/L (0.5–1.4 mg/dL). $CL_{CR}$, determined from 24-hour urine collections, averaged 94.5±25.3 ml/min with a range of 42.7–146.9 ml/min.

In the study, BCM analysis was chosen over analysis by body weight. By definition, the measurement of body weight alone does not allow the determination of fat, lean mass and water. Due to these deficiencies, methods have been developed to assess different body compartments. Body cell mass (BCM) is a heterogeneous compartment consisting of all non-adipose tissue cells, the aqueous components of adipocytes and the hematopoietic cells. BCM is distinct from fat, extracellular water and extracellular solids.

Classically, the size of the BCM in a patient has been difficult to estimate, since it is such a heterogeneous compartment. Techniques such as total body potassium content, total body nitrogen content and intracellular water volume are available at a few highly specialized clinical nutrition research centers. Their cost and sophistication, however, make them unsuitable for most everyday clinical uses.

The body cell mass (BCM) of the patients were determined using bioimpedance analysis (BIA) techniques as disclosed in Ser. No. 08/353,933, now pending, filed on Dec. 12, 1994, which is herein incorporated by reference. The analysis was accomplished using the RJL 101 bioimpedance analyzer manufactured by RJL Systems of Clinton Township, Mich. Calculation of BCM was accomplished by using Fluid and Nutrition Analysis v. 3.1 software, also marketed by RJL Systems, which incorporates the BIA formulas of Ser. No. 08/353,933.

Bioimpedance analysis was chosen for determining renal function because the machine involved is portable, operator-independent and simple to learn and operate. In addition, accuracy in the measurement of BCM by BIA are independent of such factors as a patient's age, race, gender, hydration status and disease. Furthermore, BIA has proven to be an accurate evaluator of body cell mass.

To perform BCM analysis, the bioimpedance analyzer is affixed to a patient. In the procedure, patients are asked to lie on their back on an examination table with their shoes and socks removed. Two electrodes are placed on a patient's right wrist and right ankle. A current of approximately 800 microamps at 50 kHz is then delivered. Resistance (the voltage drop of the applied current) and reactance (opposition to electric current caused by capacitance) are measured.

In accordance with the disclosure of Ser. No. 08/353,933, a human body's ionic circuit is best represented as a parallel circuit containing capacitors. In the '933 application, the optimal exponents for height, resistance and impedance were determined using a multiple regression technique after logarithmic transformation of the data. The most accurate representations for BCM in males and females were determined to be:

$$BCM=0.76[(59.06)Ht^{1.60}/Xc_p^{0.50}]+18.52(Wt)-386.66 \text{(for males)};$$

$$BCM=0.96[(1.30)Ht^{2.07}/Xc_p^{0.36}]+5.79(Wt)-230.51 \text{(for females)};$$

where:

Ht=height of the patient (cm);

$Xc_p$=parallel transformed reactance (ohms); and

Wt=weight of the patient (kg).

Predictive equations for $CL_{CR}$ based upon body composition measured through BIA were derived through multiple linear regression analysis of data obtained from patients in this study. The results show that BCM has a stronger correlation with creatinine clearance than does body weight, body mass index or fat free mass. The strongest correlation was between body cell mass index (BCMI=BCM/height$^2$) and measured $CL_{CR}$ ($CL_{CR}$=12.5(BCMI)−5.7, $r^2$=0.59, standard estimate of the error=15.7, $p<0.001$). The addition of age, gender, height or serum creatinine concentration, alone or in combination, did not improve the prediction.

Furthermore, the measured creatinine clearance determined by using BIA did not correlate with estimates made from the Cockcroft-Gault equation ($r^2$=−0.06, $p$=0.88). $CL_{CR}$ also did not correlate with the individual variables of age, serum creatinine, ideal body weight, height or sex, as relied on by the C-G equation. In a study of 10 subjects, the predicted estimates of $CL_{CR}$ overestimated the actual $CL_{CR}$ in 7 out of 10 cases, and underestimated in the remaining 30% of the subjects.

Body weight as a percent of ideal, however, correlated with creatinine clearance ($r^2$=0.18, $p<0.02$), suggesting that the C-G equation might systematically overestimate creatinine clearance in subjects below ideal weight and underestimate creatinine clearance in subjects over ideal weight. Residual analysis confirmed this impression.

These results indicate that the standard C-G equation for estimating renal function is prone to large errors in patients whose weights vary from ideal. The error is systematic in that Cockcroft-Gault estimates are high in undernourished subjects and low in obese subjects. Use of such an equation could lead to increased potential for toxicity in malnourished subjects or to underdosing in obese subjects. The likely cause for the error is that the kidneys are components of BCM, and renal function is influenced by changes in the BCM.

Even though, the use of actual weight instead of ideal weight in the C-G equation improves its accuracy, the use of BCM, especially when normalized per height$^2$, provides a better estimate of renal function, irrespective of age and sex. The lack of influence of age and sex upon renal function in the prediction suggests that these factors effect renal function indirectly, through direct effects upon BCM. The standard error of estimation of the prediction is about 17% which must be viewed in the context that the variability of a 24-hour $CL_{CR}$ is between 10 and 20%.

While the foregoing indicates the preferred embodiments of the invention claimed below, those skilled in the art will appreciate that there are variations of the inventor's disclosure which do not depart from the scope of the invention herein. For example, isotope dilution analysis, or the like, may be substituted for bioimpedance analysis. BIA may be based on modelling the human body using segmental analysis or the like. Additionally, different amperages and frequencies may be used during BIA, all of which are within the skill of those in the art to readily determine.

Other methods may be used to estimate BCM, including, but not limited to, analysis of total body potassium, intracellular water volume, and total body nitrogen. Also, different mathematical equations may be used to determine BCM from BIA other than those referred to above.

I claim:

1. A method for estimating creatinine clearance in a subject, said method comprising the steps of:

calculating a value for body cell mass of said subject; and estimating creatinine clearance of said subject as a function of said value.

2. The method of claim 1 wherein said calculating step includes the step of measuring said value using bioimpedance analysis.

3. The method of claim 1 further comprising the step of measuring the height of said subject.

4. The method of claim 3 wherein said predicting step comprises determining creatinine clearance according to the equation:

$$CL_{CR}=12.5\times(BCMI)-5.7$$

where $CL_{CR}$=creatinine clearance; and

BCMI=body cell mass (kg)/height$^2$(m$^2$).

5. A method for predicting creatinine clearance in a subject, said method comprising the steps of:

calculating the value of body cell mass of the subject using bioimpedance analysis;

measuring the height of said subject;

determining the body cell mass index of said subject; and determining creatinine clearance according to the equation:

$$CL_{CR}=12.5\times(BCMI)-5.7$$

where:

$CL_{CR}$=creatinine clearance; and

BCMI=body cell mass/height$^2$ (kg/m$^2$).

6. The method of claim 5 wherein the calculating step includes the step of determining body cell mass according to the following equations:

$$BCM=0.76[(59.06)Ht^{1.60}/Xc_p^{0.50}]+18.52(Wt)-386.66 \text{(for males)};$$

or $$BCM=0.96[(1.30)Ht^{2.07}/Xc_p^{0.36}]+5.79(Wt)-230.51 \text{(for females)};$$

where:

Ht=height (cm);

Xc$_p$ =parallel transformed reactance (ohms); and

Wt=weight (kg).

7. A method for accurately prescribing medication comprising the steps of:

determining a value for the body cell mass of a subject;

determining a value for the height of the subject;

estimating creatinine clearance of said subject from said values of body cell mass and height; and prescribing an appropriate dosage of medication in accordance with said estimated creatinine clearance.

8. The method of claim 7 wherein the step of determining said body cell mass comprises the step of using bioimpedance analysis.

9. The method of claim of claim 7 wherein said measuring of body cell mass comprises the following formulas to determine values for body cell mass:

$$BCM = 0.76[(59.06)Ht^{1.60}/Xc_p^{0.50}] + 18.52(Wt) - 386.66 \text{ (for males)};$$

or $$BCM = 32\ 0.96[(1.30)Ht^{2.07}/Xc_p^{0.36}] + 5.79(Wt) - 230.51 \text{ (for females)};$$

where:

Ht=height (cm);

Xc$_p$=parallel transformed reactance (ohms); and

Wt=weight (kg).

10. The method of claim 7 wherein the step of estimating the creatinine clearance of said subject comprises using the following formula:

$$CL_{CR} = 12.5 \times (BCMI) - 5.7$$

where:

CL$_{CR}$=creatinine clearance; and

BCMI=body cell mass/height$^2$ (kg/m$^2$).

\* \* \* \* \*

UNITED STATES PATENT AND TRADEMARK OFFICE
CERTIFICATE OF CORRECTION

PATENT NO. : 5,722,396
DATED : March 3, 1998
INVENTOR(S) : Donald P. Kotler et al.

It is certified that error appears in the above-identified patent and that said Letters Patent is hereby corrected as shown below:

Title page,
Column 2, item [56], References Cited,
Line 17, "M., O'Connell et al.," should read -- M. O'Connell et al.; --
Line 25, "*Ann. Pharmacther.*" should read -- *Ann. Pharamcother.* --.

Column 6,
Line 4, "effect" should read -- affect --.

Claims,
Column 8,
Line 4, "BCM 32 0.96" should read -- BCM = 0.96 --.

Signed and Sealed this

Second Day of October, 2001

Attest:

NICHOLAS P. GODICI
Attesting Officer    Acting Director of the United States Patent and Trademark Office